United States Patent [19]

Nohara et al.

[11] Patent Number: 4,689,333

[45] Date of Patent: Aug. 25, 1987

[54] 2-(2-PYRIDYLMETHYLTHIO (SULFINYL)) BENZIMIDAZOLES

[75] Inventors: Akira Nohara; Yoshitaka Maki, both of Kyoto, Japan

[73] Assignee: Takeda Chemical Industries, Ltd., Osaka, Japan

[21] Appl. No.: 937,193

[22] Filed: Dec. 2, 1986

Related U.S. Application Data

[63] Continuation-in-part of Ser. No. 760,568, Jul. 29, 1985, Pat. No. 4,628,098.

[30] Foreign Application Priority Data

Aug. 16, 1984 [JP] Japan ................ 59-171069

[51] Int. Cl.$^4$ ............................................. A61K 31/44
[52] U.S. Cl. .................................................... 514/338
[58] Field of Search ......................................... 514/338

[56] References Cited

U.S. PATENT DOCUMENTS

| | | | |
|---|---|---|---|
| 4,045,563 | 8/1977 | Berntsson et al. | 546/271 |
| 4,255,431 | 3/1981 | Junggren et al. | 546/271 |
| 4,472,409 | 9/1984 | Senn-Bilfinger | 546/271 |

FOREIGN PATENT DOCUMENTS

| | | |
|---|---|---|
| 5129 | 2/1982 | European Pat. Off. |
| 45200 | 2/1982 | European Pat. Off. |
| 74341 | 3/1983 | European Pat. Off. |
| 134400 | 3/1985 | European Pat. Off. |
| 150586 | 8/1985 | European Pat. Off. |
| 166287 | 1/1986 | European Pat. Off. |
| 167943 | 1/1986 | European Pat. Off. |
| 173664 | 3/1986 | European Pat. Off. |
| 2134523A | 8/1984 | United Kingdom |

*Primary Examiner*—Jane T. Fan
*Attorney, Agent, or Firm*—Wegner & Bretschneider

[57] ABSTRACT

The compound of the formula

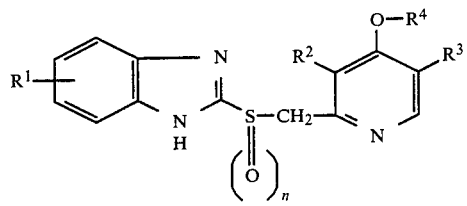

wherein $R^1$ is hydrogen, methoxy or trifluoromethyl, $R^2$ and $R^3$ are independently hydrogen or methyl, $R^4$ is a $C_{2-5}$ fluorinated alkyl and n denotes 0 or 1, or a pharmacologically acceptable salt thereof is novel, and useful for prophylaxis and therapy of digestive ulcers (e.g. gastric ulcer, duodenal ulcer) and gastritis.

10 Claims, No Drawings

2-(2-PYRIDYLMETHYLTHIO (SULFINYL)) BENZIMIDAZOLES

This is a continuation-in-part of Ser. No. 760,568, filed on July 29, 1985, now U.S. Pat. No. 4,628,098 issued Dec. 9, 1986.

This invention relates to a pharmaceutical composition containing pyridine derivatives useful as e.g. anti-ulcer agents and a method for preventing or treating digestive ulcers by administering orally the pyridine derivatives.

As pyridine derivatives having anti-ulcer activity, those disclosed in U.S. Pat. No. 4,255,431 (Japanese Unexamined Patent Laid-open No. 141783/79) and U.S. Pat. No. 4,472,409 (Japanese Unexamined Patent Laid-open No. 135881/83) etc. have been known.

However, while these known compounds have an acid-secretion-inhibiting action, their gastric mucous membrane protecting action is insufficient, thus being hardly considered satisfactory as anti-ulcer agents. Besides, these compounds are possessed of such drawbacks in the physico-chemical properties as being unstable and readily decomposed.

It is considered that gastrointestinal ulcer is induced by unbalance between aggressive factors, e.g. hydrochloric acid, pepsin, and defensive factors, e.g. mucus secretion and mucosal blood flow. Therefore, a medicine having both an action of inhibiting gastric acid secretion and an action of enhancing protection of gastric mucosa has been desired.

The present inventors diligently studied with the purpose of preparing an anti-ulcer agent having excellent actions of inhibiting gastric acid secretion, of protecting gastric mucosa and of antagonizing ulceration. They found that a certain type of pyridine derivatives meets the said purpose, and they conducted further study to accomplish the present invention.

The present invention relates to (1) A pharmaceutical composition for preventing or treating digestive ulcers or gastritis, which contains an effective amount of a compound of the formula (I)

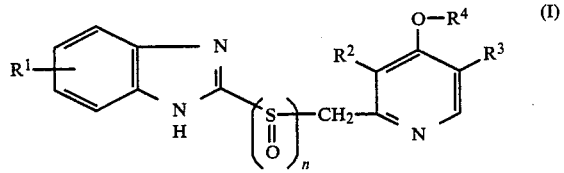

wherein $R^1$ is hydrogen, methoxy or trifluoromethyl, $R^2$ and $R^3$ are independently hydrogen or methyl, $R^4$ is a $C_{2-5}$ fluorinated alkyl and n denotes 0 or 1, or a pharmacologically acceptable salt thereof, and pharmacologically acceptable carriers, and (2) A method for preventing or treating digestive ulcers or gastritis, which comprises administering a compound of the formula (I) or a phramcologically acceptable salt thereof, and pharmacologically acceptable carriers.

The compound (I) or its phramcologically acceptable salt can be produced by allowing a compound of the formula (II)

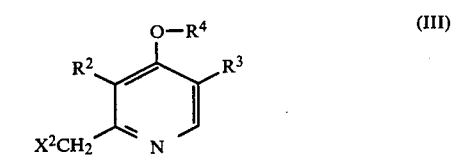

wherein $R^1$ is of the same meaning as defined above, to react with a compound of the formula (III)

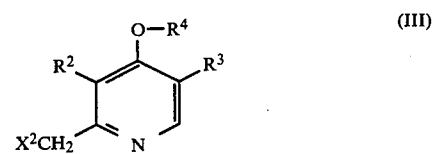

wherein $R^2$, $R^3$ and $R^4$ are of the same meaning as defined above, one of $X^1$ and $X^2$ is SH and the other is a leaving group and, when necessary, by subjecting the reaction product to oxidation.

In the above formulae, $C_{2-5}$ fluorinated alkyl groups shown by $R^4$ are exemplified by 2,2,2-trifluoroethyl, 2,2,3,3,3-pentafluoropropyl, 2,2,3,3-tetrafluoropropyl, 1-(trifluoromethyl)-2,2,2-trifluoroethyl, 2,2,3,3,4,4,4-heptafluorobutyl and 2,2,3,3,4,4,5,5-octafluoropentyl.

Examples of the leaving groups $X^1$ and $X^2$ in the above formulae are halogen, preferably chlorine, bromine or iodine, or a reactive esterified hydroxy group, e.g. an arylsulfonyloxy, for example, phenylsulfonyloxy or tosyloxy, or $C_{1-4}$ alkylsulfonyloxy, for example, methanesulfonyloxy, or an organic phosphoryloxy, for example, diphenylphosphoryloxy, dibenzylphosphoryloxy or di-$C_{1-4}$ alkylphosphoryloxy and the like.

$R^1$ may be located at 4- or 5-position, and preferably at 5-position.

A sulfide derivative (I) (n=0), among the object compounds of this invention, can be prepared by allowing a compound (II) to react with a compound (III). It is convenient to conduct this reaction in the presence of a base. The base is exemplified by alkali metal hydride e.g. sodium hydride and potassium hydride; alkali metal e.g. metallic sodium; sodium alcoholate e.g. sodium methoxide and sodium ethoxide; alkali metal carbonate e.g. potassium carbonate and sodium carbonate; and organic amines e.g. triethylamine. The solvent used for the reaction is exemplified by alcohols e.g. methanol and ethanol, as well as dimethylformamide. The amount of a base used for the reaction is usually in a little excess to the equivalent, but it may be in a large excess. Specifically, it is about 1–10 equivalents, more preferably about 1–4 equivalents. The reaction temperature ranges usually from about 0° C. to about the boiling point of the solvent then used, more preferably from about 20° C. to about 80° C. The reaction time ranges from about 0.2 to about 24 hours, more preferably from about 0.5 to about 2 hours.

A sulfinyl derivative (I) (n=1), which is also among the object compounds of this invention, can be prepared by subjecting a compound (I) (n=0) to oxidation. The oxidizing agent to be employed here is exemplified by peracid e.g. m-chloroperbenzoic acid, peracetic acid, trifluoroperacetic acid and permaleic acid, or sodium bromite or sodium hypochlorite or hydrogen peroxide. The solvent used for the reaction is exemplified by halogenated hydrocarbon e.g. chloroform and dichloromethane, ethers e.g. tetrahydrofuran and dioxane, amides e.g. dimethylformamide, alcohols, e.g. methanol, ethanol, propanol, and t-butanol or water, and these solvents may used singly or in admixture. The oxidizing agent is used preferably in approximately equivalent or a little excess amount relative to the compound (I) ($n=0$). Specifically, it is about 1 to about 3 equivalents, more preferably about 1–1.5 equivalent. The reaction temperature ranges from that under ice-cooling to about the boiling point of the solvent then employed, usually from that under ice-cooling to room temperature, more preferably from about 0° C. to about 10° C. The reaction time usually ranges from about 0.1 to about 24 hours, more preferably from about 0.1 to about 4 hours.

The object compound (I) produced by the above reaction can be isolated and purified by conventional means e.g. recrystallization and chromatography.

The compound (I) of this invention may be led to pharmacologically acceptable salts thereof by per se conventional means, the salts being exemplified by hydrochloride, hydrobromide, hydroiodide, phosphate, nitrate, sulfate, acetate and citrate.

Among the compounds (I), those of $n=0$ give stable salts, while those of $n=1$ may exist as an aqueous solution though unstable.

The process of preparing the starting material (III) is described as follows.

Process (1)

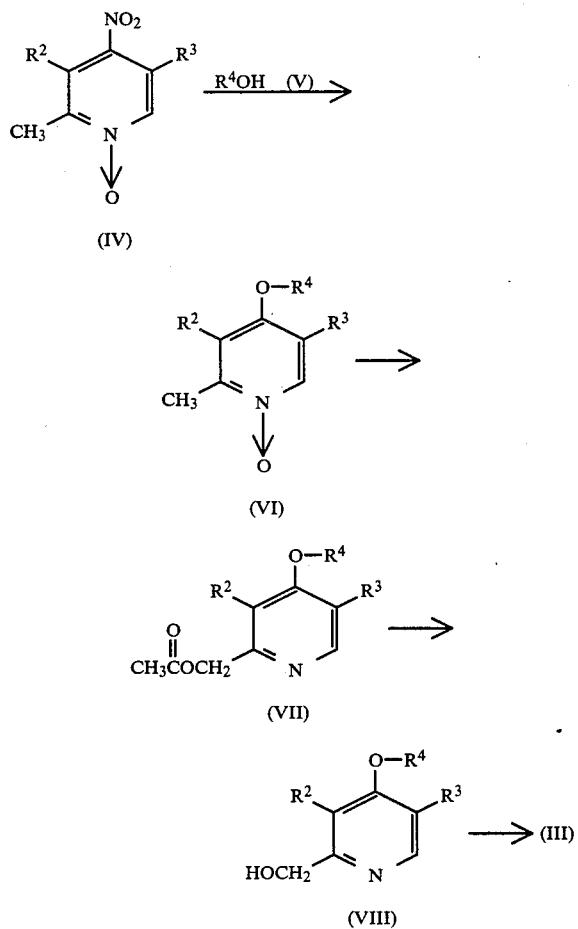

A nitro compound of the formula (IV) [wherein $R^2$ and $R^3$ are of the same meaning as defined above] is allowed to react with an alcohol derivative $R^4OH$ (V) [wherein $R^4$ is of the same meaning as defined above] in the presence of a base to give an alkoxy derivative of the formula (VI) [wherein $R^2$, $R^3$ and $R^4$ are of the same meaning as defined above]. The base is exemplified by alkali metal e.g. lithium, sodium and potassium; alkali metal hydride e.g. sodium hydride and potassium hydride; alcoholate e.g. potassium t-butoxide and sodium propoxide; alkali metal carbonate or hydrogen carbonate e.g. potassium carbonate, lithium carbonate, sodium carbonate, potassium hydrogen carbonate and sodium hydrogen carbonate; or alkali hydroxide e.g. sodium hydroxide and potassium hydroxide. The solvent used for the reaction is exemplified by, besides $R^4OH$ itself, ethers such as tetrahydrofuran and dioxane as well as ketones such as acetone and methyl ethyl ketone, acetonitrile, dimethylformamide and hexamethylphosphoric acid triamide. The reaction temperature is suitably selected within the range from those under ice-cooling to those near the boiling point of the solvent used. The reaction time ranges usually from about 1 to about 48 hours.

The thus-obtained compound (VI) is subjected to heating (about 80° to about 120° C.) in the presence of acetic anhydride singly or together with a mineral acid e.g. sulfuric acid and perchloric acid to give a 2-acetoxymethylpyridine derivative of the formula (VII) [wherein $R^2$, $R^3$ and $R^4$ are of the same meaning as defined above]. The reaction time ranges usually from about 0.1 to about 10 hours.

Then, the compound (VII) is subjected to alkali-hydrolysis to give a 2-hydroxymethyl pyridine derivative of the formula (VIII) [wherein $R^2$, $R^3$ and $R^4$ are of the same meaning as defined above]. The alkali is exemplified by sodium hydroxide, potassium hydroxide, potassium carbonate and sodium carbonate. The solvent used for the reaction is exemplified by methanol, ethanol and water. The reaction temperature ranges usually from about 20° C. to about 60° C. The reaction time is within the range of from about 0.1 to about 2 hours.

The compound (VIII) is further subjected to reaction with a chlorinating agent such as thionyl chloride, or an esterifying agent, e.g. an organic sulfonic acid chloride such as methanesulfonyl chloride or p-toluenesulfonyl chloride, or an organic phosphoric acid chloride such as diphenylphosphoryl chloride to give the compound (III). The amount of the chlorinating agent used for the reaction is usually in equivalent to a large excess relative to the compound (VIII). The solvent used for the reaction is exemplified by chloroform, dichloromethane and tetrachloroethane. The reaction temperature is usually within the range of from about 20° C. to about 80° C., and the reaction time is about 0.1 to about 2 hours.

The amount of the organic sulfonic acid chloride or organic phosphoric acid chloride used for the reaction is usually in equivalent to a little excess, and the reaction is usually conducted in the presence of a base. The base is exemplified by organic base e.g. triethylamine and tributylamine, or inorganic base e.g. sodium carbonate, potassium carbonate and sodium hydrogen carbonate. The amount of a base used for the reaction is usually in equivalent to a little excess. The solvent used for the reaction is exemplified by chloroform, dichloromethane, carbon tetrachloride or acetonitrile. The reaction temperature ranges usually from that under ice-cooling to about the boiling point of the solvent then used. The reaction time ranges usually from a few minutes to a few hours. It is usually preferable to use the thus-produced compound (III) immediately for the reaction with a compound (II).

Process (2)

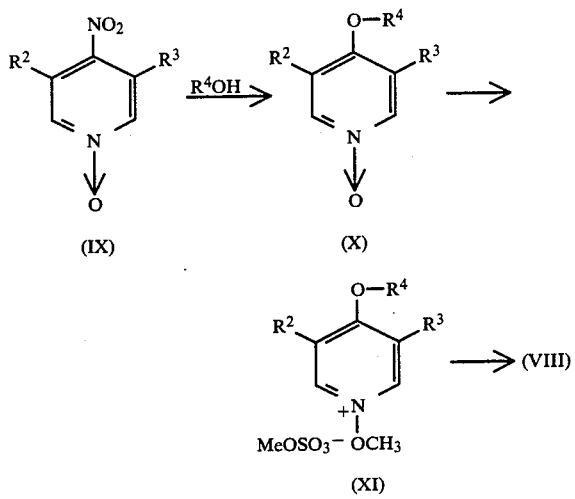

By a reaction similar to the above-described process (1), a compound of the formula (IX) [wherein $R^2$ and $R^3$ are of the same meaning as defined above] is led to a compound of the formula (X) [wherein $R^2$, $R^3$ and $R^4$ are of the same meaning as defined above].

Then, the compound (X) is subjected to methylation with dimethyl sulfate to give a compound of the formula (XI) [wherein $R^2$, $R^3$ and $R^4$ are of the same meaning as defined above]. The reaction can be conducted usually without solvent. The reaction temperature ranges from about 100° C. to about 120° C., and the reaction time is within the range of from about 0.1 to about 4 hours.

Further, the compound (XI) is allowed to react with a radical source such as ammonium persulfate or any other persulfate in methanol to give the above-mentioned compound (VIII). The reaction temperature is within the range of from about 20° C. to about 80° C., and the reaction time ranges from about 0.5 to about 4 hours.

Pharmacological actions of the compounds of the present invention are described as follows.

As the models of gastrointestinal ulcers, restraint and water-immersion stress-induced ulcer, indomethacin-induced ulcer and ethanol-induced gastric mucosal lesions have been used. However, as a model mimicking human gastric ulcer, indomethacin-induced gastric antral ulcer was reported in "Gastroenterology" (Satoh et al. 81, p. 719, 1981), which is considered to be of value as an experimental model. Therefore, the following are data of anti-ulcer actions of the object compounds (I) and of some representable known compounds, on the ulcer model in the above-mentioned literature reference.

Experimental Method

Male Sprague-Dawley rats of 7-weeks old were fasted for 24 hours. These animals were administered test compounds into stomach by using a gastric tube. After 30 minutes, indomethacin, 30 mg/kg subcutaneously, was administered. During 30-90 minutes after the administration of indomethacin, these animals had free access to chow pellets (Japan Clea, CE-2). At 5 hours after the administration of indomethacin, 1 ml of 1% Evans blue was injected to the animals via the tail vein, followed by sacrificing these animals with carbon dioxide gas. The stomach was removed together with the lower part of esophagus and the duodenum. The esophagus was clipped, 10 ml of 1% formalin solution was instilled into the stomach from the duodenum, and then the duodenum was clipped. The whole stomach was immersed in 1% formalin solution. About 15 minutes later, the stomachs were opened along the greater curvature. The area of the lesions which occurred in the gastric antral mucosa was measured under a dissecting microscope with a square-grid eye piece (x10). The sum total of the individual lesions in each animal was measured, and the average value per group was calculated. Based on the difference between the average value of each group and that of the control group, the inhibition rate was determined. The test compound and indomethahacin were suspended in a 5% gum arabic solution, respectively and administered in a volume of 2 ml/kg.

Experimental Results:

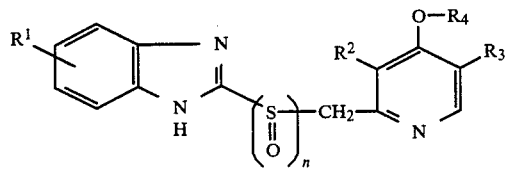

| $R^1$ | $R^2$ | $R^3$ | $R^4$ | n | Anti-ulcer action[a] $ID_{50}$ (mg/kg, p.o.) |
|---|---|---|---|---|---|
| H | H | H | $CH_2CF_3$ | 1 | 2.4 |
| H | $CH_3$ | H | $CH_2CF_3$ | 1 | <1.0 |
| H | H | H | $CH_2CF_2CF_3$ | 1 | 1.3 |
| H | $CH_3$ | H | $CH_2CF_2CF_3$ | 1 | <1.0 |
| H | H | H | $CH_2CF_2CF_2H$ | 1 | 1.3 |
| H | $CH_3$ | H | $CH_2CF_2CF_2H$ | 1 | <1.0 |
| H | $CH_3$ | H | $CH_2CF_2CF_3$ | 0 | 3.7 |
| 5-$OCH_3$ | $CH_3$ | $CH_3$ | $CH_3$*1 | | 21.0 |
| 5-$CF_3$ | $CH_3$ | H | $CH_3$*2 | | 5.5 |

*1 The compound disclosed in Example 23 of U.S. Pat. No. 4,255,431 (Japanese Unexamined Patent Laid-open No. 141783/1979)
*2 The compound disclosed in Example 3 of U.S. Pat. No. 4,472,409 (Japanese Unexamined Patent Laid-open No. 135881/1983)
[a] Using 6 rats per group, each of the test compounds was administered in a dose of 1, 3, 10 and 30 mg/kg to determine $ID_{50}$.

As shown by the above data, the compounds of this invention have superior anti-ulcer action as compared with known compounds by about 1.5-20 times or more. Besides, the compound (I) of this invention shows excellent actions of inhibiting gastric acid secretion, protecting gastric mucous membrane and preventing ulceration.

Regarding about the toxicity of the compound (I) of this invention, oral administration of the compound employed for the experiment of anti-ulceration (compound of $R^1$=H, $R^2$=$CH_3$, $R^3$=H, $R^4$=$CH_2CF_2CF_3$, n=1) to mice even in a dose of 2000 mg/kg caused no fatal effect; thus the compound (I) is low in toxicity.

As described in the foregoing, the compound (I) of this invention has an anti-ulcer action, a gastric acid secretion controlling action and mucous membrane protecting action, furthermore is of low toxicity and is relatively stable as a chemical substance. The compound (I) of this invention can thus be used for prophylaxis and therapy of digestive ulcers (e.g. gastric ulcer, duodenal ulcer) and gastritis in mammalian animals (e.g. mouse, rat, rabbit, dog, cat and man).

For the treatment of digestive ulcer or gastritis in mammals, the compounds (I) of this invention can be orally given in the dosage form such as capsules, tablets, granules and powders obtained by general techniques well known in the pharmaceutical art, for example, by mixing with pharmacologically acceptable carriers, such as excipients (e.g. lactose, starch, sucrose, etc.), disintegrators (e.g. starch, carboxymethyl-cellulose calcium, etc.), lubricants (e.g. magnesium stearate, talc, etc.), binders (e.g. hydroxypropyl-cellulose, hydroxypropylmethyl-cellulose, macrogol, etc.), and so on.

The mixing ratio (by weight) of the carriers to the compounds (I) is about 0.01 to 200, preferably about 0.01 to 100. The dose ranges from about 0.01 to 30 mg/kg/day, more preferably from about 0.1 to 3 mg/kg/day.

Incidentally, the compound of this invention (I) (n=0) is useful as a starting material for preparing the compound (I) (n=1).

The processes of producing the starting compounds to be employed in the method of this invention as well as those of producing the compound (I) of this invention are specifically explained by the following Reference Examples and Working Examples.

REFERENCE EXAMPLE 1

In 2,2,3,3-tetrafluoropropanol (10 ml) was dissolved 2,3-dimethyl-4-nitropyridine-1-oxide (2 g). To the solution was added potassium t-butoxide (1.6 g) little by little at room temperature. The mixture was then heated at 80°–90° C. for 22 hours. The reaction solution was diluted with water, which was subjected to extraction with chloroform. The extract was dried on magnesium sulfate, and then concentrated. The concentrate was chromatographed on a column of silica gel (70 g). Elution was conducted with methanol-chloroform (1:10), and then subjected to recrystallization from ethyl acetate-hexane to yield 2.6 g of 2,3-dimethyl-4-(2,2,3,3-tetrafluoropropoxy)pyridine-1-oxide as colorless needles, m.p. 138°–139° C.

After the manner above, compounds (VI) were prepared from compounds (IV).

| | | Compound (VI) | |
|---|---|---|---|
| $R^2$ | $R^3$ | $R^4$ | Melting point (°C.) |
| H | H | $CH_2CF_3$ | 148–150 |
| $CH_3$ | $CH_3$ | $CH_2CF_3$ | 138–139 |

REFERENCE EXAMPLE 2

A mixture of 2,3-dimethyl-4-nitropyridine-1-oxide (2.0 g), methyl ethyl ketone (30 ml), 2,2,3,3,3-pentafluoropropanol (3.05 ml), anhydrous potassium carbonate (3.29 g) and hexamethyl phosphoric acid triamide (2.07 g) was heated at 70°–80° C. for 4.5 days under stirring, then insolubles were filtered off. The filtrate was concentrated, to which was added water. The mixture was subjected to extraction with ethyl acetate. The extract solution was dried on magnesium sulfate, followed by removing the solvent by evaporation. The residue was chromatographed on a column of silica gel (50 g), eluted with chloroform-methanol (10:1), and recrystallized from ethyl acetate-hexane to yield 2.4 g of 2,3-dimethyl-4-(2,2,3,3,3-pentafluoropropoxy)pyridine-1-oxide as colorless needles, m.p. 148°–149° C.

By this process, compounds (VI) were prepared from starting compounds (IV).

| | | Compound (VI) | |
|---|---|---|---|
| $R^2$ | $R^3$ | $R^4$ | Melting point (°C.) |
| $CH_3$ | H | $CH_2CF_3$ | 131.0–131.5 |
| H | $CH_3$ | $CH_2CF_3$ | 153–154 |
| H | H | $CH_2CF_2CF_3$ | 79–81 |
| H | $CH_3$ | $CH_2CF_2CF_3$ | 140–142 |
| H | H | $CH_2CF_2CF_2H$ | Oily |
| H | $CH_3$ | $CH_2CF_2CF_2H$ | 143.5–144.5 |
| $CH_3$ | H | $CH_2CF_2CF_2H$ | 138–139 |

REFERENCE EXAMPLE 3

Concentrated sulfuric acid (two drops) was added to a solution of 2,3-dimethyl-4-(2,2,3,3-tetrafluoropropoxy)pyridine-1-oxide (2.6 g) in acetic anydride (8 ml). The mixture was stirred at 110° C. for 4 hours, which was then concentrated. The residue was dissolved in methanol (20 ml), to which was added sodium hydroxide (1.2 g) dissolved in water (5 ml). The mixture was stirred at room temperature for 30 minutes, which was concentrated. To the residue was added water, and the mixture was subjected to extraction with ethyl acetate. The extract was dried on magnesium sulfate, followed by removal of the solvent by evaporation. The residue was chromatographed on a column of silica gel (50 g), eluted with chloroform-methanol (10:1), and recrystallized from isopropyl ether to yield 1.6 g of 2-hydroxymethyl-3-methyl-4-(2,2,3,3-tetrafluoropropoxy)pyridine as yellow crystals, m.p. 67°–68° C.

By this process, compounds (VIII) were prepared from compounds (VI).

| | | Compound (VIII) | |
|---|---|---|---|
| $R^2$ | $R^3$ | $R^4$ | Melting point (°C.) |
| H | H | $CH_2CF_3$ | Oily |
| $CH_3$ | H | $CH_2CF_3$ | 93.5–94.0 |
| H | H | $CH_2CF_2CF_3$ | Oily |
| $CH_3$ | H | $CH_2CF_2CF_3$ | Oily |
| H | $CH_3$ | $CH_2CF_2CF_3$ | 87–89 |
| H | H | $CH_2CF_2CF_2H$ | 88–89 |
| H | $CH_3$ | $CH_2CF_2CF_2H$ | 98–99 |
| $CH_3$ | H | $CH_2CF_2CF_2H$ | 67–68 |

REFERENCE EXAMPLE 4

To a solution of 3,5-dimethyl-4-nitropyridine-1-oxide (2.0 g) in 2,2,3,3,3-pentafluoropropanol (10 g) was added at 0° C. little by little potassium t-butoxide (2 g) over 15 minutes. The mixture was stirred at 60° C. for 18 hours. To the reaction mixture was added chloroform, which was subjected to filtration with celite. The filtrate was chromatographed on a column of silica gel (80 g), eluted with ethyl acetate-hexane (1:1), then with 20% methanol-ethyl acetate, and recrystallized from ether-hexane to yield 2.6 g of 3,5-dimethyl-4-(2,2,3,3,3-pentafluoropropoxy)pyridine-1-oxide as crystals, m.p. 89°–91° C.

By this process, compounds (X) were prepared from compounds (IX).

| | | Compound (X) | |
|---|---|---|---|
| $R^2$ | $R^3$ | $R^4$ | Melting point (°C.) |
| $CH_3$ | H | $CH_2CF_3$ | 82–94 |

-continued

| | | Compound (X) | |
|---|---|---|---|
| $R^2$ | $R^3$ | $R^4$ | Melting point (°C.) |
| $CH_3$ | $CH_3$ | $CH_2CF_3$ | 138–139 |

REFERENCE EXAMPLE 5

A mixture of 3,5-dimethyl-4-(2,2,3,3,3-pentafluoropropoxy)pyridine-1-oxide (2.5 g) and dimethyl sulfate (1 ml) was heated at 120° C. for 30 minutes, to which was then added methanol (12.5 ml). To the mixture was added dropwise at 80° C. ammonium persulfate (4.3 g) dissolved in water (20 ml)-methanol (10 ml) over 30 minutes, which was stirred for further 30 minutes. The resultant solution was concentrated. To the residue was added ice, which was neutralized with sodium carbonate, followed by extraction with chloroform. The extract was dried on sodium sulfate, followed by removing the solvent by evaporation to give 2.2 g of 3,5-dimethyl-2-hydroxymethyl-4-(2,2,3,3,3-pentafluoropropoxy)pyridine as an oily substance.

By this process, compounds (VIII) were prepared from compounds (X).

| | | Compound (VIII) | |
|---|---|---|---|
| $R^2$ | $R^3$ | $R^4$ | Melting point (°C.) |
| H | $CH_3$ | $CH_2CF_3$ | 116–119 |
| $CH_3$ | $CH_3$ | $CH_2CF_3$ | 62–63 |

EXAMPLE 1

To a solution of 2-hydroxymethyl-3-methyl-4-(2,2,3,3,3-pentafluoropropoxy)pyridine (350 mg) in chloroform (10 ml) was added thionyl chloride (0.2 ml). The mixture was refluxed for 30 minutes, which was then concentrated. The residue was dissolved in methanol (5 ml). The solution was added to a mixture of 2-mercaptobenzimidazole (200 mg), 28% sodium methoxide solution (1 ml) and methanol (6 ml), which was refluxed for 30 minutes. From the resultant was removed methanol by evaporation. To the residue was added water, which was subjected to extraction with ethyl acetate. The extract was washed with a dilute sodium hydroxide solution, followed by drying on magnesium sulfate. From the resultant was removed the solvent by evaporation. The residue was then chromatographed on a column of silica gel (20 g), eluted with ethyl acetate-hexane (2:1), and then recrystallized from ethyl acetate-hexane to yield 370 mg of 2-[3-methyl-4-(2,2,3,3,3-pentafluoropropoxy)-pyrid-2-yl]methylthiobenzimidazole-½ hydrate as colorless plates, m.p. 145°–146° C.

By this process, compounds (I) (n=0) were prepared by allowing compounds (II) to react with compounds (III).

| | | | Compound (I) (n=0) | |
|---|---|---|---|---|
| $R^1$ | $R^2$ | $R^3$ | $R^4$ | Melting point (°C.) |
| H | H | H | $CH_2CF_3$ | 138–139 |
| H | $CH_3$ | H | $CH_2CF_3$ | 149–150 |
| H | H | $CH_3$ | $CH_2CF_3$ | 168–170 |
| H | $CH_3$ | $CH_3$ | $CH_2CF_3$ | 151.5–152.0 |
| H | H | H | $CH_2CF_2CF_3$ | 125–126 |
| H | H | $CH_3$ | $CH_2CF_2CF_3$ | 151–152 |
| H | H | H | $CH_2CF_2CF_2H$ | Oily *3 |
| H | $CH_3$ | H | $CH_2CF_2CF_2H$ | 134–135 |

-continued

| | | | Compound (I) (n=0) | |
|---|---|---|---|---|
| $R^1$ | $R^2$ | $R^3$ | $R^4$ | Melting point (°C.) |
| H | H | $CH_3$ | $CH_2CF_2CF_2H$ | 148–149 |
| H | $CH_3$ | $CH_3$ | $CH_2CF_2CF_3$ | 158–160 |
| *4 5-$CF_3$ | $CH_3$ | H | $CH_2CF_3$ | 92–93 |
| 5-$OCH_3$ | $CH_3$ | H | $CH_2CF_3$ | 159–160 |
| 5-$OCH_3$ | H | H | $CH_2CF_3$ | 152–153 |

*3 NMR spectrum $(CDCl_3)\delta$:4.35(S),4.39(t,t,J = 1.5 and 12 Hz), 5.98 (1H,t,t,J = 52.5 and 4 Hz), 6.81 (1H,d,d,J = 2 and 6 Hz) 6.95 (1H,d,J = 2 Hz), 7.1–7.3 (2H,m), 7.4–7.7 (2H,m), 8.50 (1H,d,J = 6 Hz)
*4: ½$H_2O$ (crystal water)

EXAMPLE 2

To a solution of 2-[3-methyl-4-(2,2,3,3,3-pentafluoropropoxy)pyrid-2-yl]methylthiobenzimidazole (2.2 g) in chloroform (20 ml) was added dropwise under ice-cooling over a period of 30 minutes m-chloroperbenzoic acid (1.3 g) dissolved in chloroform (15 ml). The solution was washed with a saturated aqueous solution of sodium hydrogen carbonate, then dried on magnesium sulfate, and concentrated. The residue was chromatographed on a column of silica gel (50 g), eluted with ethyl acetate, and then recrystallized from acetone-isopropyl ether to give 1.78 g of 2-[3-methyl-4-(2,2,3,3,3-pentafluoropropoxy)pyrid-2-yl]methylsulfinylbenzimidazole as pale yellow prisms, m.p. 161°–163° C. (decomp.).

By this process, compounds (I) (n=1) were prepared from compounds (I) (n=0).

| | | | Compound (I) (n=1) | |
|---|---|---|---|---|
| $R^1$ | $R^2$ | $R^3$ | $R^4$ | Melting point (°C.) |
| H | H | H | $CH_2CF_3$ | 176–177 |
| H | $CH_3$ | H | $CH_2CF_3$ | 178–182(d) |
| H | H | $CH_3$ | $CH_2CF_3$ | 175–177(d) |
| H | $CH_3$ | $CH_3$ | $CH_2CF_3$ | 177–178(d) |
| H | H | H | $CH_2CF_2CF_3$ | 148–150(d) |
| H | H | $CH_3$ | $CH_2CF_2CF_3$ | 145–148(d) |
| H | H | H | $CH_2CF_2CF_2H$ | 132–133 |
| H | $CH_3$ | H | $CH_2CF_2CF_2H$ | 147–148(d) |
| H | H | $CH_3$ | $CH_2CF_2CF_2H$ | 136–139(d) |
| H | $CH_3$ | $CH_3$ | $CH_2CF_2CF_3$ | 157–159 |
| 5-$CF_3$ | $CH_3$ | H | $CH_2CF_3$ | 161–162(d) |
| 5-$OCH_3$ | $CH_3$ | H | $CH_2CF_3$ | 140.5–142(d) |
| 5-$OCH_3$ | H | H | $CH_2CF_3$ | 162–163(d) |

(Note)
(d): decomposition

EXAMPLE 3

| Tablet | |
|---|---|
| (1) Compound A* | 30 mg |
| (2) Corn starch | 20 mg |
| (3) Lactose | 85.2 mg |
| (4) Micro crystalline cellulose | 60 mg |
| (5) Light anhydrous silicic acid | 1.8 mg |
| (6) Magnesium stearate | 3.0 mg |
| (7) Magnesium hydroxide | 30 mg |
| (8) L-Cysteine | 20 mg |
| | 250 mg (One tablet) |

*Compound A: 2-[3-methyl-4-(2,2,2-trifluoroethoxy)-pyrid-2-yl]methylsulfinylbenzimidazole (Production method)

The above ingredients (1), (2), (3), (7) and (8) were mixed and then mixed with half of the amount of above ingredients (4), (5) and (6). The blended mixture was compressed and formed using a drying-granulator (Roller Compacter, Freund Industrial, Co., Ltd., Japan). After this slug was comminuted in a mortar and sieved by a 16-mesh sieve, to the granule obtained was added the remaining amount of the ingredients (4), (5) and (6) and mixed together. Then, the mixture was compressed using a rotary-tabletting machine (Kikusui Seisakusho Ltd., Japan) to obtain tablets (250 mg per one tablet).

(Dosage)

Dosage is one tablet/adult after meal (one time/day).

EXAMPLE 4

| Capsule | |
|---|---|
| (1) Compound A | 30 mg |
| (2) Corn starch | 40 mg |
| (3) Lactose | 74 mg |
| (4) Hydroxypropylcellulose | 6 mg |
| (5) Magnesium carbonate | 50 mg |
| (6) Water | (0.1 ml) |
| | 200 mg |

(Production method)

The above ingredients (1) to (5) were mixed together. To the resulting mixture was added water. The mixture, after being kneaded, was dried under vacuum at 40° C. for 16 hours. The dried mass was comminuted in a mortar and sieved by a 16-mesh sieve to obtain granules. By filling these granules in a gelatin capsule (No. 3), a capsule was produced.

(Dosage)

Dosage is one capsule/adult after meal (one time/day).

What we claim is:

1. A phramaceutical composition for preventing or treating digestive ulcers or gastritis, which contains an effective amount of a compound of the formula

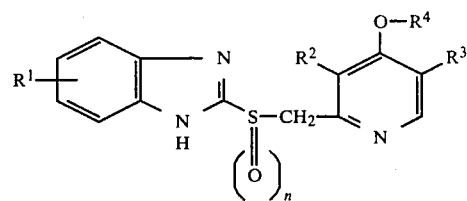

wherein $R^1$ is hydrogen, methoxy or trifluoromethyl, $R^2$ and $R^3$ are independently hydrogen or methyl, $R^4$ is a $C_{2-5}$ fluorinated alkyl and n denotes 0 or 1, or a pharmacologically acceptable salt thereof, and pharmacologically acceptable carriers.

2. A phamaceutical composition according to claim 1, wherein $R^1$ is hydrogen or trifluoromethyl.

3. A pharmaceutical composition according to claim 1, wherein $R^3$ is hydrogen.

4. A pharmaceutical composition according to claim 1, wherein n is 1.

5. A phamaceutical composition according to claim 1, wherein $R^1$ and $R^3$ are hydrogen, $R^2$ is methyl, $R^4$ is 2,2,2-trifluoroethyl and n is 1.

6. A method for preventing or treating digestive ulcers or gastritis, which comprises administering a compound of the formula

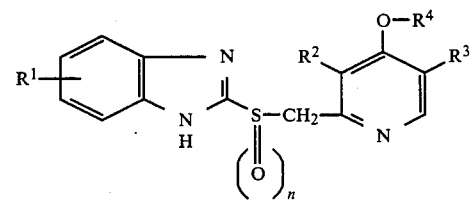

wherein $R^1$ is hydrogen, methoxy or trifluoromethyl, $R^2$ and $R^3$ are independently hydrogen or methyl, $R^4$ is a $C_{2-5}$ fluorinated alkyl and n denotes 0 or 1, or a pharmacologically acceptable salt thereof, and pharmacologically acceptable carriers.

7. A method according to claim 6, wherein $R^1$ is hydrogen or trifluoromethyl.

8. A method according to claim 6, wherein $R^3$ is hydrogen.

9. A method according to claim 6, wherein n is 1.

10. A method according to claim 6, wherein $R^1$ and $R^3$ are hydrogen, $R^2$ is methyl, $R^4$ is 2,2,2-trifluoroethyl and n is 1.

* * * * *